United States Patent
Barker (10) Patent No.: US 9,078,793 B2
(45) Date of Patent: Jul. 14, 2015

(54) HOOK-ENGAGEABLE LOOP FASTENERS AND RELATED SYSTEMS AND METHODS

(75) Inventor: James R. Barker, Francestown, NH (US)

(73) Assignee: Velcro Industries B.V., Willemstad (CW)

( * ) Notice: Subject to any disclaimer, the term of this patent is extended or adjusted under 35 U.S.C. 154(b) by 423 days.

(21) Appl. No.: 13/525,508

(22) Filed: Jun. 18, 2012

(65) Prior Publication Data

US 2013/0052399 A1 Feb. 28, 2013

Related U.S. Application Data

(60) Provisional application No. 61/527,353, filed on Aug. 25, 2011.

(51) Int. Cl.
| | |
|---|---|
| D04H 1/54 | (2012.01) |
| D04H 13/00 | (2006.01) |
| B29C 65/02 | (2006.01) |
| B32B 37/04 | (2006.01) |
| B32B 43/00 | (2006.01) |
| B32B 5/00 | (2006.01) |
| A61F 13/62 | (2006.01) |
| A44B 18/00 | (2006.01) |

(52) U.S. Cl.
CPC ............. *A61F 13/62* (2013.01); *A44B 18/0003* (2013.01); *D04H 13/00* (2013.01)

(58) Field of Classification Search
CPC ....... D04H 1/46; D04H 13/00; D04H 13/003; D04H 13/005; D04H 13/007; B32B 5/26; B32B 27/00; B32B 37/04; B29C 65/18; B29C 66/43; B29C 66/919; A61F 16/62; A61F 16/622; A61F 13/627; A44B 18/0003
USPC ................................... 156/148, 308.2, 309.3
See application file for complete search history.

(56) References Cited

U.S. PATENT DOCUMENTS

| | | | |
|---|---|---|---|
| RE18,001 E | 3/1931 | Rayner | |
| 2,706,324 A | 4/1955 | Cogovan | |

(Continued)

FOREIGN PATENT DOCUMENTS

| | | |
|---|---|---|
| DE | 101 39 842 | 4/2003 |
| EP | 0 341 993 | 11/1989 |

(Continued)

OTHER PUBLICATIONS

International Search Report and Written Opinion of PCT/US2012/042907 mailed Nov. 2, 2012 (18 pp).
Dilo Group, "Market Leadership in Nonwovens Technology", Pakistan Textile Journal, date unknown (2 pages).
Dilo, "Engineering Excellence in Needle Looms!", Hyperpunch—The Solution for Fine and Quality Fleeces, Synthetic Leather, Spunbondeds, Papermachine Felts!, date unknown (2 pages).
Purdy, Terry, Dilo Inc., Needle Punching Benefits from Elliptical Needle Paths, date unknown (13 pages).

(Continued)

*Primary Examiner* — Sing P Chan
(74) *Attorney, Agent, or Firm* — Fish & Richardson P.C.

(57) ABSTRACT

A method of making a sheet-form loop product can include placing a layer of staple fibers on a first side of a substrate, the layer of staple fibers including first staple fibers and second staple fibers that are intermingled with one another, where a diameter of the smallest circle capable of circumscribing one of the second staple fibers is greater than a diameter of the smallest circle capable of circumscribing one of the first staple fibers; needling substantially only the first fibers of the layer through the substrate by penetrating the substrate with needles that drag portions of the first fibers through the substrate during needling, leaving exposed loops of the first fibers extending from a second side of the substrate; and anchoring the loops of the first fibers by fusing the second fibers to each other on the first side of the substrate.

17 Claims, 9 Drawing Sheets

(56) References Cited

U.S. PATENT DOCUMENTS

| | | |
|---|---|---|
| 3,047,444 A | 7/1962 | Harwood |
| 3,348,992 A | 10/1967 | Cochran, II |
| 3,408,417 A | 10/1968 | Sogawa et al. |
| 3,496,260 A | 2/1970 | Guenther et al. |
| 3,535,178 A | 10/1970 | Parlin et al. |
| 3,577,607 A | 5/1971 | Ikoma et al. |
| 3,674,618 A | 7/1972 | Spann |
| 3,694,867 A | 10/1972 | Stumpf |
| 3,704,191 A | 11/1972 | Buresh et al. |
| 3,705,065 A | 12/1972 | Stumpf |
| 3,708,361 A | 1/1973 | Stumpf |
| 3,819,462 A | 6/1974 | Starr et al. |
| 3,822,162 A | 7/1974 | Stumpf |
| 3,940,525 A | 2/1976 | Ballard |
| 3,949,128 A | 4/1976 | Ostermeier |
| 3,950,587 A | 4/1976 | Colijn et al. |
| 4,001,472 A | 1/1977 | Thomas et al. |
| 4,010,302 A | 3/1977 | Anderson et al. |
| 4,035,533 A | 7/1977 | Chambley |
| 4,116,892 A | 9/1978 | Schwarz |
| 4,131,704 A | 12/1978 | Erickson et al. |
| 4,154,885 A | 5/1979 | Tecl et al. |
| 4,154,889 A | 5/1979 | Platt |
| 4,192,086 A | 3/1980 | Sichak |
| 4,223,059 A | 9/1980 | Schwarz |
| 4,258,094 A | 3/1981 | Benedyk |
| 4,258,097 A | 3/1981 | Benedyk |
| 4,295,251 A | 10/1981 | Tatham et al. |
| 4,315,965 A | 2/1982 | Mason et al. |
| 4,320,167 A | 3/1982 | Wishman |
| 4,324,824 A | 4/1982 | Narens et al. |
| 4,342,802 A | 8/1982 | Pickens, Jr. et al. |
| 4,363,845 A | 12/1982 | Hartmann |
| 4,377,889 A | 3/1983 | Tatham et al. |
| 4,379,189 A | 4/1983 | Platt |
| 4,389,442 A | 6/1983 | Pickens, Jr. et al. |
| 4,389,443 A | 6/1983 | Thomas et al. |
| 4,391,866 A | 7/1983 | Pickens, Jr. et al. |
| 4,418,104 A | 11/1983 | Kiyomura et al. |
| 4,439,476 A | 3/1984 | Guild |
| 4,446,189 A | 5/1984 | Romanek |
| 4,451,314 A | 5/1984 | Knoke et al. |
| 4,451,315 A | 5/1984 | Miyazaki |
| 4,490,425 A | 12/1984 | Knoke et al. |
| 4,521,472 A | 6/1985 | Gold |
| 4,536,439 A | 8/1985 | Forsten |
| 4,600,605 A | 7/1986 | Nakai et al. |
| 4,600,618 A | 7/1986 | Raychok, Jr. et al. |
| 4,609,581 A | 9/1986 | Ott |
| 4,645,699 A | 2/1987 | Neveu |
| 4,654,246 A | 3/1987 | Provost et al. |
| 4,750,443 A | 6/1988 | Blaustein et al. |
| 4,761,318 A | 8/1988 | Ott et al. |
| 4,770,917 A | 9/1988 | Tochacek et al. |
| 4,931,343 A | 6/1990 | Becker et al. |
| 4,973,326 A | 11/1990 | Wood et al. |
| 5,032,122 A | 7/1991 | Noel et al. |
| 5,066,289 A | 11/1991 | Polski |
| 5,080,951 A | 1/1992 | Guthrie |
| 5,144,730 A | 9/1992 | Dilo |
| 5,216,790 A | 6/1993 | Eschenbach |
| 5,254,194 A | 10/1993 | Ott et al. |
| 5,256,231 A | 10/1993 | Gorman et al. |
| 5,265,954 A | 11/1993 | Keil |
| 5,304,162 A | 4/1994 | Kuen |
| 5,307,616 A | 5/1994 | Goineau et al. |
| 5,320,890 A | 6/1994 | Anton et al. |
| 5,326,612 A | 7/1994 | Goulait |
| 5,379,501 A | 1/1995 | Goineau |
| 5,380,313 A | 1/1995 | Gonlait et al. |
| 5,380,580 A | 1/1995 | Rogers et al. |
| 5,382,461 A | 1/1995 | Wu |
| 5,383,872 A | 1/1995 | Roessler et al. |
| 5,386,595 A | 2/1995 | Kuen et al. |
| 5,391,424 A | 2/1995 | Kolzer |
| 5,403,302 A | 4/1995 | Roessler et al. |
| 5,407,439 A | 4/1995 | Goulait |
| 5,407,722 A | 4/1995 | Peake, III et al. |
| 5,417,902 A | 5/1995 | Bennie et al. |
| 5,423,789 A | 6/1995 | Kuen |
| 5,447,590 A | 9/1995 | Gilpatrick |
| 5,449,530 A | 9/1995 | Peake, III et al. |
| 5,459,991 A | 10/1995 | Nabeshima et al. |
| 5,470,417 A | 11/1995 | Goulait |
| 5,476,702 A | 12/1995 | Datta et al. |
| 5,500,268 A | 3/1996 | Billarant |
| 5,515,583 A | 5/1996 | Higashinaka |
| 5,518,795 A | 5/1996 | Kennedy et al. |
| 5,531,732 A | 7/1996 | Wood |
| 5,542,942 A | 8/1996 | Kline et al. |
| 5,547,531 A | 8/1996 | Allen et al. |
| 5,554,239 A | 9/1996 | Datta et al. |
| 5,569,233 A | 10/1996 | Goulait |
| 5,571,097 A | 11/1996 | Seth |
| 5,595,567 A | 1/1997 | King et al. |
| 5,599,601 A | 2/1997 | Polski et al. |
| 5,603,708 A | 2/1997 | Seth |
| 5,605,729 A | 2/1997 | Mody et al. |
| 5,611,789 A | 3/1997 | Seth |
| 5,611,791 A | 3/1997 | Gorman et al. |
| 5,614,232 A | 3/1997 | Torigoe et al. |
| 5,614,281 A | 3/1997 | Jackson et al. |
| 5,615,460 A | 4/1997 | Weirich et al. |
| 5,616,155 A | 4/1997 | Kronzer |
| 5,616,394 A | 4/1997 | Gorman et al. |
| 5,620,779 A | 4/1997 | Levy et al. |
| 5,622,578 A | 4/1997 | Thomas |
| 5,624,427 A | 4/1997 | Bergman et al. |
| 5,630,896 A | 5/1997 | Corbin et al. |
| 5,643,397 A | 7/1997 | Gorman et al. |
| 5,647,864 A | 7/1997 | Allen et al. |
| 5,654,070 A | 8/1997 | Billarant |
| 5,660,911 A | 8/1997 | Tesch |
| 5,669,593 A | 9/1997 | Kirchner |
| 5,669,900 A | 9/1997 | Bullwinkel et al. |
| 5,669,901 A | 9/1997 | LaFortune et al. |
| 5,672,222 A | 9/1997 | Eschenbach |
| 5,685,756 A | 11/1997 | Noda |
| 5,686,163 A | 11/1997 | Tsubata et al. |
| 5,692,949 A | 12/1997 | Sheffield et al. |
| 5,695,845 A | 12/1997 | Ogawa et al. |
| 5,699,593 A | 12/1997 | Jackson |
| 5,707,707 A | 1/1998 | Burnes et al. |
| 5,707,906 A | 1/1998 | Eschenbach |
| 5,722,968 A | 3/1998 | Datta et al. |
| 5,732,453 A | 3/1998 | Dilo et al. |
| 5,736,214 A | 4/1998 | Billarant |
| 5,759,926 A | 6/1998 | Pike et al. |
| 5,763,041 A | 6/1998 | Leak et al. |
| 5,766,723 A | 6/1998 | Oborny et al. |
| 5,773,120 A | 6/1998 | Deka et al. |
| 5,786,060 A | 7/1998 | Takahashi et al. |
| 5,814,390 A | 9/1998 | Stokes et al. |
| 5,830,298 A | 11/1998 | Jackson |
| 5,843,057 A | 12/1998 | McCormack |
| 5,858,515 A | 1/1999 | Stokes et al. |
| 5,866,222 A | 2/1999 | Seth et al. |
| 5,888,607 A | 3/1999 | Seth et al. |
| 5,891,547 A | 4/1999 | Lawless |
| 5,904,793 A | 5/1999 | Gorman et al. |
| 5,931,823 A | 8/1999 | Stokes et al. |
| 5,945,215 A | 8/1999 | Bersted et al. |
| 5,953,797 A | 9/1999 | Provost et al. |
| 5,962,102 A | 10/1999 | Sheffield et al. |
| 5,962,112 A | 10/1999 | Haynes et al. |
| 5,964,742 A | 10/1999 | McCormack et al. |
| 5,997,981 A | 12/1999 | McCormack et al. |
| 6,051,094 A | 4/2000 | Melbye et al. |
| 6,086,984 A | 7/2000 | DiMaggio, Jr. et al. |
| 6,087,279 A | 7/2000 | Laun |
| 6,093,665 A | 7/2000 | Sayovitz et al. |
| 6,129,879 A | 10/2000 | Bersted et al. |
| 6,129,964 A | 10/2000 | Seth |
| 6,158,097 A | 12/2000 | Dilo |

(56) References Cited

U.S. PATENT DOCUMENTS

| | | | |
|---|---|---|---|
| 6,161,269 A | 12/2000 | Dilo et al. |
| 6,162,522 A | 12/2000 | Deka et al. |
| 6,192,556 B1 | 2/2001 | Kikko et al. |
| 6,195,850 B1 | 3/2001 | Melbye et al. |
| 6,248,276 B1 | 6/2001 | Parellada et al. |
| 6,265,053 B1 | 7/2001 | Kronzer et al. |
| 6,280,670 B1 | 8/2001 | Buzzell et al. |
| 6,329,016 B1 | 12/2001 | Shepard et al. |
| 6,342,285 B1 | 1/2002 | Shepard et al. |
| 6,355,759 B1 | 3/2002 | Sherman et al. |
| 6,368,444 B1 | 4/2002 | Jameson et al. |
| 6,410,138 B2 | 6/2002 | Mleziva et al. |
| 6,454,989 B1 | 9/2002 | Neely et al. |
| 6,489,004 B1 | 12/2002 | Martin et al. |
| 6,537,935 B1 | 3/2003 | Seth et al. |
| 6,558,602 B1 | 5/2003 | Melbye et al. |
| 6,598,276 B2 | 7/2003 | Shepard et al. |
| 6,638,611 B2 | 10/2003 | Seth |
| 6,642,160 B1 | 11/2003 | Takahashi |
| 6,642,429 B1 | 11/2003 | Carter et al. |
| 6,645,611 B2 | 11/2003 | Seth |
| 6,660,202 B2 | 12/2003 | Shepard et al. |
| 6,686,303 B1 | 2/2004 | Haynes et al. |
| 6,703,086 B2 | 3/2004 | Kronzer et al. |
| 6,709,996 B2 | 3/2004 | Mleziva et al. |
| 6,716,511 B2 | 4/2004 | Bersted et al. |
| 6,740,385 B2 | 5/2004 | Gardner et al. |
| 6,756,327 B2 | 6/2004 | Martin |
| 6,783,834 B2 | 8/2004 | Shepard et al. |
| 6,849,142 B1 | 2/2005 | Goulait |
| 6,869,659 B2 | 3/2005 | Shepard et al. |
| 6,893,525 B1 | 5/2005 | Schmidt et al. |
| 6,948,221 B2 | 9/2005 | Fuchs |
| 6,955,847 B1 | 10/2005 | Itou et al. |
| 6,991,843 B2 | 1/2006 | Parellada et al. |
| 7,052,638 B2 | 5/2006 | Clarner et al. |
| 7,117,571 B2 | 10/2006 | Dilo |
| 7,156,937 B2 | 1/2007 | Provost et al. |
| 7,275,290 B2 | 10/2007 | Clarner et al. |
| 7,276,642 B2 | 10/2007 | Belau |
| 7,282,251 B2 | 10/2007 | Provost et al. |
| 7,465,366 B2 | 12/2008 | Provost et al. |
| 7,547,469 B2 | 6/2009 | Provost et al. |
| 7,562,426 B2 | 7/2009 | Barker et al. |
| 2001/0051253 A1 | 12/2001 | Tai et al. |
| 2003/0077430 A1 | 4/2003 | Grimm et al. |
| 2003/0101549 A1 | 6/2003 | Wang et al. |
| 2003/0119404 A1 | 6/2003 | Belau et al. |
| 2004/0020579 A1 | 2/2004 | Durrance et al. |
| 2004/0022993 A1 | 2/2004 | Wildeman |
| 2004/0072491 A1 | 4/2004 | Gillette et al. |
| 2004/0131820 A1 | 7/2004 | Turner |
| 2004/0157036 A1 | 8/2004 | Provost et al. |
| 2004/0163221 A1 | 8/2004 | Shepard et al. |
| 2004/0229008 A1 | 11/2004 | Hoying |
| 2005/0196580 A1 | 9/2005 | Provost et al. |
| 2005/0196581 A1 | 9/2005 | Provost et al. |
| 2005/0196583 A1 | 9/2005 | Provost et al. |
| 2005/0208259 A1 | 9/2005 | Provost et al. |
| 2005/0217092 A1 | 10/2005 | Barker et al. |
| 2005/0281976 A1 | 12/2005 | Curro et al. |
| 2006/0105664 A1 | 5/2006 | Zafiroglu |
| 2006/0183389 A1 | 8/2006 | Zafiroglu |
| 2006/0225258 A1 | 10/2006 | Barker et al. |
| 2007/0178273 A1 | 8/2007 | Provost et al. |
| 2008/0113152 A1 | 5/2008 | Provost et al. |
| 2008/0305291 A1 | 12/2008 | Nakaoka et al. |
| 2008/0305297 A1 | 12/2008 | Barker et al. |
| 2008/0305704 A1 | 12/2008 | Provost et al. |
| 2009/0203280 A9 | 8/2009 | Provost et al. |
| 2009/0208699 A1 | 8/2009 | Miyauchi et al. |

FOREIGN PATENT DOCUMENTS

| | | |
|---|---|---|
| EP | 0 211 564 | 2/1992 |
| EP | 0 482 749 | 4/1992 |
| EP | 0 325 473 | 3/1993 |
| EP | 0 604 731 | 7/1994 |
| EP | 0 619 085 | 10/1994 |
| EP | 0 765 616 | 4/1997 |
| EP | 0 780 066 | 6/1997 |
| EP | 0 780 505 | 6/1997 |
| EP | 0 598 085 | 7/1997 |
| EP | 0 597 075 | 4/1998 |
| EP | 0 882 828 | 12/1998 |
| EP | 0 937 420 | 8/1999 |
| EP | 0 726 977 | 6/2000 |
| EP | 0 862 868 | 6/2001 |
| EP | 1 132 511 | 9/2001 |
| EP | 0 861 137 | 1/2002 |
| EP | 1 279 348 | 1/2003 |
| EP | 1 156 767 | 10/2004 |
| EP | 1 113 099 | 3/2006 |
| EP | 1 689 259 | 12/2008 |
| GB | 1 228 421 | 4/1971 |
| GB | 1228431 | 4/1971 |
| GB | 2 068 023 | 8/1981 |
| GB | 2 285 093 | 6/1995 |
| JP | 6-33359 | 2/1994 |
| JP | 06-123061 | 5/1994 |
| JP | 7-171011 | 7/1995 |
| JP | 08-27657 | 1/1996 |
| JP | 09 003755 | 1/1997 |
| JP | 09-195154 | 7/1997 |
| JP | 09-195155 | 7/1997 |
| JP | 09-241961 | 9/1997 |
| JP | 10-146207 | 6/1998 |
| JP | 10-151005 | 6/1998 |
| JP | 2971332 | 11/1999 |
| JP | 2000-314065 | 11/2000 |
| JP | 2001-212 | 1/2001 |
| JP | 2001-8713 | 1/2001 |
| JP | 3134709 | 2/2001 |
| JP | 2001-207369 | 8/2001 |
| JP | 2001-514346 | 9/2001 |
| JP | 2002-10807 | 1/2002 |
| JP | 2003-265207 | 9/2003 |
| JP | 2004-194730 | 7/2004 |
| JP | 3855084 | 12/2006 |
| JP | 3877842 | 2/2007 |
| WO | WO92/01401 | 2/1992 |
| WO | WO95/17111 | 6/1995 |
| WO | WO 95/20335 | 8/1995 |
| WO | WO98/33410 | 8/1998 |
| WO | WO99/11452 | 3/1999 |
| WO | WO00/40793 | 7/2000 |
| WO | WO00/42964 | 7/2000 |
| WO | WO01/80680 | 1/2001 |
| WO | WO02/100207 | 12/2002 |
| WO | WO03/051251 | 6/2003 |
| WO | WO2004/019305 | 3/2004 |
| WO | WO2004/049853 | 6/2004 |
| WO | WO2004/058118 | 7/2004 |
| WO | WO2004/058497 | 7/2004 |
| WO | WO2004/059061 | 7/2004 |
| WO | WO2004/059117 | 7/2004 |
| WO | WO2005/037006 | 4/2005 |
| WO | WO2006/110575 | 10/2006 |
| WO | WO2006/110598 | 10/2006 |

OTHER PUBLICATIONS

Website: http://www.inda.org/pubs/c-papers/np00-toc.html. Inda.org, Needlepunch 2000 conference paper listing, retrieved Sep. 24, 2007. 2 Pages.

Narejo, D., et al, "Advances in Needlepunching", GFR, Jun./Jul. 2002, pp. 18-21.

International Search Report and Written Opinion; Application No. PCT/US2012/042901; mailed Dec. 21, 2012; 12 pages.

HOOK-ENGAGEABLE LOOP FASTENERS AND RELATED SYSTEMS AND METHODS

CROSS-REFERENCE TO RELATED APPLICATIONS

This application claims the benefit of U.S. Application Ser. No. 61/527,353, filed on Aug. 25, 2011, which is incorporated by reference herein.

TECHNICAL FIELD

This invention relates to hook-engageable loop fasteners and related systems and methods.

BACKGROUND

In woven and knit loop materials, loop-forming filaments or yarns are included in the structure of a fabric to form upstanding loops for engaging hooks. The cost of woven and knit loop fasteners of this type is a major factor limiting the extent of use of such fasteners.

SUMMARY

In one aspect of the invention, a method of making a sheet-form loop product includes placing a layer of staple fibers on a first side of a substrate, the layer of staple fibers including first staple fibers and second staple fibers that are intermingled with one another, where a diameter of the smallest circle capable of circumscribing one of the second staple fibers is greater than a diameter of the smallest circle capable of circumscribing one of the first staple fibers; needling substantially only the first fibers of the layer through the substrate by penetrating the substrate with needles that drag portions of the first fibers through the substrate during needling, leaving exposed loops of the first fibers extending from a second side of the substrate; and anchoring the loops of the first fibers by fusing the second fibers to each other on the first side of the substrate.

Embodiments can include one or more of the following features.

In some embodiments, the needles are forked needles having a recess width configured to inhibit the second fibers from being needled through the substrate.

In some embodiments, the recess width is less than 110 percent of the diameter of the smallest circle capable of circumscribing one of the second staple fibers.

In some embodiments, the diameter of the smallest circle capable of circumscribing one of the second staple fibers is at least about 90 percent of the recess width of the needles.

In some embodiments, the diameter of the smallest circle capable of circumscribing one of the second staple fibers is about 90-150 percent of the recess width of the needles.

In some embodiments, the diameter of the smallest circle capable of circumscribing one of the second staple fibers is at least about 100 percent of the recess width of the needles.

In some embodiments, the diameter of the smallest circle capable of circumscribing one of the second staple fibers is about 100-150 percent of the recess width of the needles.

In some embodiments, the diameter of the smallest circle capable of circumscribing one of the first staple fibers is about 15-35 microns.

In some embodiments, the diameter of the smallest circle capable of circumscribing one of the second staple fibers is about 50-75 microns.

In some embodiments, the needles are 38-42 gauge forked needles. In some embodiments, the needles include 40 gauge forked needles having a recess width of 70 microns, the diameter of the smallest circle capable of circumscribing one of the first staple fibers is about 17 microns, and the diameter of the smallest circle capable of circumscribing one of the second staple fibers is about 65 microns.

In some embodiments, the first fibers include polyester and the second fibers include polypropylene.

In some embodiments, the layer of staple fibers includes no more than 50 percent of second fibers.

In some embodiments, no more than 20 second fibers per square inch are needled through the substrate.

In some embodiments, a total number of loops formed on the second side of the substrate includes no more than 10 percent loops formed of second fibers.

In some embodiments, the method further includes selecting needles based on the first and second staple fibers of the layer of staple fibers to be placed on the substrate.

In some embodiments, the needles are selected to capture the first fibers in a recess of the needles and to not capture the second fibers in the recess of the needles.

In some embodiments, the melting temperature of the first fibers is higher than the melting temperature of the second fibers.

In some embodiments, a difference between the melting temperature of the first fibers and the melting temperature of the second fibers is at least about 15 degrees Fahrenheit.

In some embodiments, the melting temperature of the second fibers is at least about 235 degrees Fahrenheit.

In some embodiments, anchoring the loops includes melting the second fibers.

In some embodiments, melting the second fibers includes melting the second fibers to form a network of bonding sites.

In some embodiments, anchoring the loops includes bonding the second fibers to portions of the first fibers and to the substrate.

In some embodiments, the first fibers and second fibers are not fixed to the substrate or each other until needled.

In some embodiments, needling substantially only the first fibers through the substrate and anchoring fibers forming the loops forms loops sized and constructed to be releasably engageable by a field of hooks for hook-and-loop fastening.

In some embodiments, the substrate includes a nonwoven web.

In some embodiments, the nonwoven web includes a spunbond web.

In some embodiments, the nonwoven web includes filaments formed of a polymer selected from the group consisting of polyesters, polyamides, polyolefins, and blends and copolymer thereof.

In another aspect of the invention, a sheet-form loop product includes a substrate and a layer of staple fibers including first fibers and second fibers disposed on a first side of the substrate, exposed loops of substantially only the first fibers extending from a second side of the substrate, with bases of the loops being anchored on the first side of the substrate, where a diameter of the smallest circle capable of circumscribing one of the second fibers is larger than a diameter of the smallest circle capable of circumscribing one of the first fibers.

Embodiments can include one or more of the following features.

In some embodiments, the first and second fibers are fused together.

In some embodiments, the diameter of the smallest circle capable of circumscribing one of the first fibers is about 15-35 microns.

In some embodiments, the diameter of the smallest circle capable of circumscribing one of the second fibers is about 50-75 microns.

In some embodiments, the first fibers include polyester and the second fibers include polypropylene.

In some embodiments, no more than 20 loops of second fibers per square inch are formed on the first side of the substrate.

In some embodiments, a total number of loops formed on the second side the substrate includes no more than 10 percent loops formed of second fibers.

In some embodiments, the melting temperature of the first fibers is higher than the melting temperature of the second fibers.

In some embodiments, a difference between the melting temperature of the first fibers and the melting temperature of the second fibers is at least about 15 degrees Fahrenheit.

In some embodiments, the melting temperature of the second fibers is at least about 235 degrees Fahrenheit.

In some embodiments, the loops are anchored to the first side of the substrate by a network of bonding sites.

In some embodiments, the network of bonding sites includes discrete regions of melted portions of the second fibers.

In some embodiments, the second fibers on the first side are fused directly to one another.

In some embodiments, the loops of first fibers are substantially unbonded on the second side of the web.

In some embodiments, the loops are sized and constructed to be releasably engageable by a field of hooks for hook-and-loop fastening.

In some embodiments, the substrate includes a nonwoven web.

In some embodiments, the nonwoven web includes a spunbond web.

Embodiments can include one or more of the following advantages.

Methods described herein can be used to form hook-engageable loop fastener products that are relatively inexpensive, lightweight, drapeable and strong with good peel strength.

Needling substantially only the first smaller fibers through the substrate helps to increase (e.g., maximize) the number of larger second fibers that remain on the back side of the substrate after the needling process. By increasing the number of second fibers, which are used primarily for bonding, on the back side of the substrate during lamination, a network of bonding sites can be formed to reduce (e.g., minimize) the amount of bonding material required to anchor the loops formed of the first fibers. As opposed to a continuous lamination along the entire backside of the substrate, anchoring the loops by forming a network of bonding sites allows the first fibers and loops to move flexibly and substantially independent of each other which further increases the drapeability of the loop product. Bonding the loop material by creating a network of bond sites also reduces the amount of materials required to manufacture loop fastener products resulting in a lighter and less expensive loop fastener product.

By using forked needles that are sized to capture substantially only the smaller, first fibers, which are used primarily to form loops and not for bonding, it is typically ensured that the larger second fibers, which are used for bonding, will typically remain on the back side of the substrate during needling. Increasing (e.g., maximizing) the number of larger second fibers that remain on the back side of the substrate enables a sufficient number of bonds to be created along the back side of the substrate to anchor the loops while reducing the amount of second fibers required as compared to many known loop material manufacturing techniques.

Other features, objects, and advantages of the invention will be apparent from the description and drawings, and from the claims.

DETAILED DESCRIPTION

In some aspects of the invention, methods of forming hook-engageable loop fastener products include placing a layer of first and second staple fibers on a first side of a substrate, where the second staple fibers have a larger maximum or average diameter than the first staple fibers. The methods further include needling substantially only the first fibers of the layer through the substrate by penetrating the substrate with needles that drag portions of the first fibers through the substrate during needling such that exposed loops of the first fibers are left extending from a second side of the substrate, and anchoring the loops of the first fibers by fusing the second fibers to each other on the first side of the substrate. Such methods can be used to produce hook-engageable fastener products that have more bonding fibers that remain on the backside of the fastener product and fewer bonding fibers that are needled through the substrate. As a result, the number of bonding fibers that remain on the back side of the substrate for lamination is increased (e.g., maximized), which means fewer bonding fibers are typically required to form the loop materials described herein as compared to certain conventional methods. Consequently, the total number of fibers required to form the loop materials can be reduced, resulting in a more drapeable, lighter weight, and less expensive loop fastener product.

Figure 1:
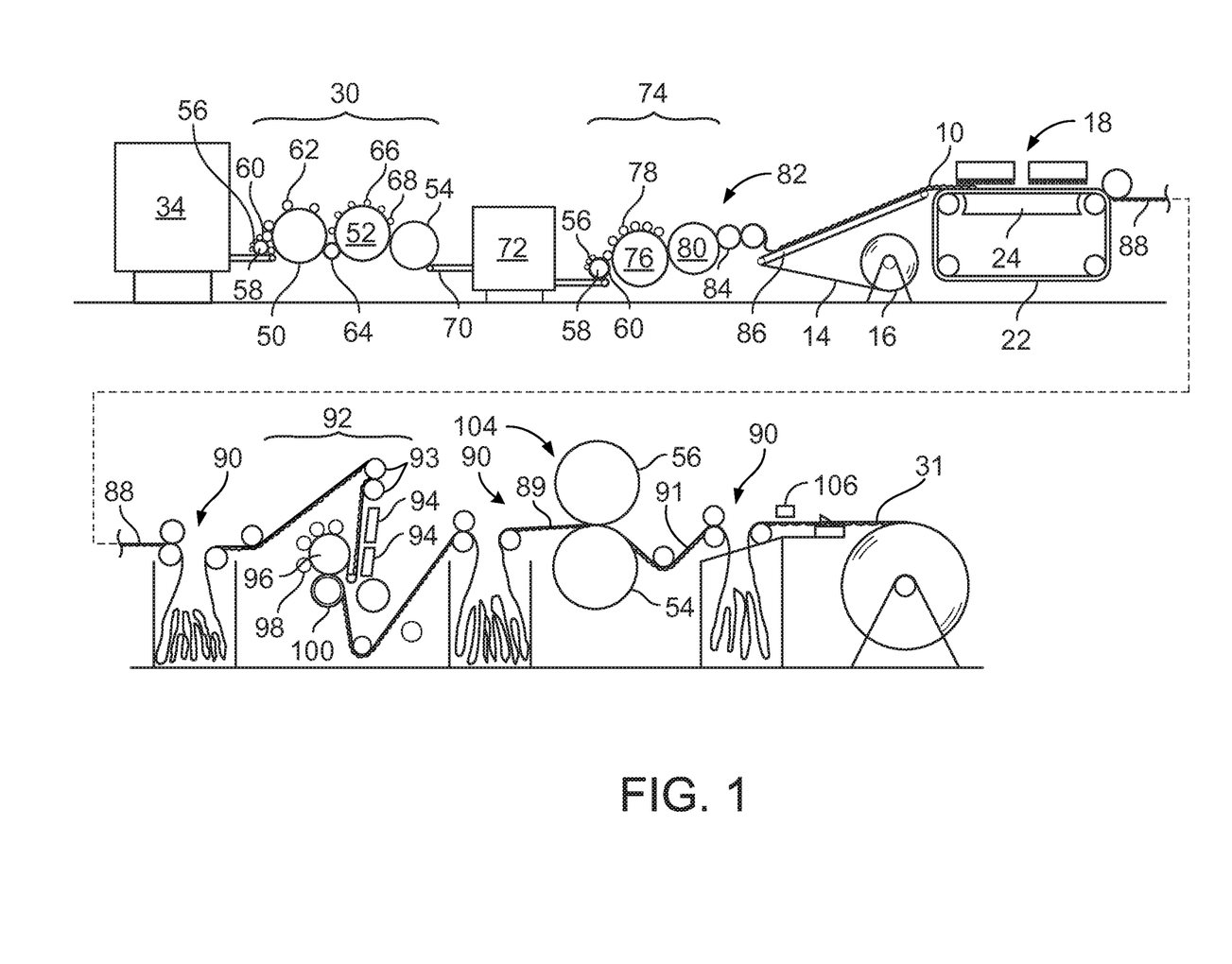
FIG. 1 is a diagrammatic view of a process for forming hook-engageable loop fastener products.

FIG. 1 illustrates a machine and process for producing an inexpensive hook-engageable touch fastener product 31. Beginning at the upper left end of FIG. 1, a carded and cross-lapped layer of first and second staple fibers 10 is created by two carding stages with intermediate cross-lapping. Weighed portions of the first and second staple fibers are fed to a first carding station 30 by a card feeder 34.

The first fibers are typically a 3 denier per filament (dpf) non-bonding polyester fiber having a mean diameter of approximately 17 microns that are about a four-inch (100 millimeters) staple length. The mean diameter can be determined by measuring the diameter of the fiber at three or more points along the fiber and averaging those measured diameters. The first fibers have a round cross-sectional shape and are crimped at about 7.5 crimps per inch (3 crimps per centimeter). To withstand melting during subsequent lamination, the first fibers have a melting temperature of approximately 495 degrees Fahrenheit (257 degrees Celsius). Suitable polyester fibers are available from Auriga Polymers of Wilmington, Del.

The second fibers are a 30 dpf bonding polypropylene fiber having a mean diameter of approximately 67 microns that are about a three-inch (75 millimeters) staple length. The fibers have a round cross-sectional shape and are crimped at about 7.5 crimps per inch (3 crimps per centimeter). For bonding, the second fibers typically have a melting temperature that is lower than the melting temperature of the first fibers by at least 15 degrees Fahrenheit (8 degrees Celsius) so that the second fibers will melt during subsequent lamination while the first fibers will remain substantially unmelted, especially on the front side where the loops are formed. In certain embodiments, the melting temperature of the second fibers is approximately 285 degrees Fahrenheit (140 degrees Celsius). Suitable polypropylene fibers are available from Asota GmbH of Linz, Austria.

As discussed below, the first and second fibers are chosen to have different diameters so that during needling, substantially only the smaller, non-bonding first fibers will be captured by a forked needle and needled through the substrate to form loops. Due to their large size and the inability of the forked needle to typically capture them, the second fibers tend to remain on the back side of the substrate and are melted later during lamination to bond and anchor the loops of first fibers. Typically, the first and second fibers are combined to form an approximate mass ratio of 4:1, first fibers to second fibers.

The carding station 30 includes a 36-inch breast roll 50, a 60-inch breaker main 52, and a 50-inch breaker doffer 54. The first card feedroll drive includes 3-inch feedrolls 56 and a 3-inch cleaning roll on a 13-inch lickerin roll 58. An 8-inch angle stripper 60 transfers the fiber to breast roll 50. There are three 8-inch worker roll sets 62 on the breast roll 50, and a 16-inch breast doffer 64 feeds the breaker main 52, against which seven 8-inch worker sets 66 and a flycatcher 68 run. The carded fibers are combed onto a conveyer 70 that transfers the single fiber layer into a cross-lapper 72.

Before cross-lapping, the carded fibers still appear in bands or streaks of single fiber types, corresponding to the fibrous balls fed to carding station 30 from the different feed bins. Cross-lapping, which normally involves a 90-degree reorientation of line direction, overlaps the fiber layer upon itself and is adjustable to establish the width of fiber layer fed into a second carding station 74. In this example, the cross-lapper output width is set to approximately equal the width of the carrier into which the fibers will be needled. Cross-lapper 72 may have a lapper apron that traverses a floor apron in a reciprocating motion. The cross-lapper 72 lays carded webs of, for example, about 80 inch (2.0 meter) width and about one-half inch (1.3 centimeter) thickness on the floor apron to build up several layers of criss-crossed web, forming a layer of, for instance, about 80 inches (2.0 meters) in width and about 4 inches (10 centimeters) in thickness, that includes four double layers of carded web.

During carding, the fibers are separated and combed into a cloth-like mat consisting primarily of parallel fibers. With nearly all of its fibers extending in the carding direction, the mat has some strength when pulled in the carding direction but almost no strength when pulled in the carding cross direction, as cross direction strength results only from a few entanglements between fibers. During cross-lapping, the carded fiber mat is laid in an overlapping zigzag pattern, creating a mat 10 of multiple layers of alternating diagonal fibers. The diagonal layers, which extend in the carding cross direction, extend more across the apron than they extend along its length. Cross-lapping the web before the second carding process provides several tangible benefits. For example, it enhances the blending of the fiber composition during the second carding stage. It also allows for relatively easy adjustment of web width and basis weight, simply by changing cross-lapping parameters.

The second carding station 74 takes the cross-lapped mat of fibers and cards them a second time. The feedroll drive consists of two 3-inch feed rolls and a 3-inch cleaning roll 56 on a 13-inch lickerin 58, feeding a 60-inch main roll 76 through an 8-inch angle stripper 60. The fibers are worked by six 8-inch worker rolls 78, the last five of which are paired with 3-inch strippers. A 50-inch finisher doffer 80 transfers the carded web to a condenser 82 having two 8-inch condenser rolls 84, from which the web is combed onto a non-woven carrier sheet 14 fed from a spool 16. The condenser typically increases the basis weight of the web and reduces the orientation of the fibers to remove directionality in the strength or other properties of the finished product.

The carrier sheet 14 is typically a nonwoven web, such as a spunbond web. Spunbond webs, and certain other suitable nonwoven webs, include continuous filaments that are entangled and fused together at their intersections (e.g., by hot calendaring). In some embodiments, for example, the carrier sheet 14 has a basis weight that ranges from 10-100 grams per square meter (gsm). One preferred spunbond web is commercially available from Oxco, Inc., Charlotte, N.C. under the tradename POLYON A017P79WT1. This material is a point bonded 100% polyester spunbond having a basis weight of 17 gsm (0.5 ounces per square yard (osy)). While maintaining proper structural requirements, the carrier sheet 14 is also lightweight and inexpensive as compared to materials used to form many woven and knit loop products. To optimize anchoring of the loops during subsequent lamination, it is desirable that the second fibers fuse not only to themselves and to the first fibers on the back side of the carrier sheet 14, but also to the filaments of the carrier sheet 14. Suitable carrier sheet materials include nylons, polyesters, polyamides, polypropylenes, EVA, and their copolymers.

The carrier sheet 14 may be supplied as a single continuous length, or as multiple, parallel strips. For particularly wide webs, it may be necessary or cost effective to introduce two or more parallel sheets, either adjacent or slightly overlapping. The parallel sheets may be unconnected or joined along a mutual edge.

From the second carding station 74, the carded, uniformly blended layer of fibers from condenser 82 is carried up conveyor 86 on carrier sheet 14 and into needling station 18 in the form of a mat 10. As the fiber layer or mat 10 enters the needling station, it has no stability other than what may have been imparted by carding and cross-lapping. In other words, the fibers are not pre-needled or felted prior to reaching a subsequent needling station 18. In this state, the fiber layer or mat 10 is not suitable for spooling or accumulating.

In the needling station 18, the carrier sheet 14 and fiber layer 10 are needle-punched from the fiber side. Forked needles are guided through a stripping plate above the fibers, and draw substantially only the smaller, first fibers through the carrier sheet 14 to form loops on the opposite side.

During needling, the carrier sheet 14 is supported on a bed of bristles extending from a driven support belt or brush apron 22 that moves with the carrier sheet 14 through the needling station 18. Reaction pressure during needling is provided by a stationary reaction plate 24 underlying the support belt or brush apron 22. The needling station 18 typically needles the fiber-covered carrier sheet 14 with an overall penetration density of about 80 to 160 punches per square centimeter. During needling, the thickness of the carded fiber layer 10 only decreases by about half, as compared with felting processes in which such a fiber layer thickness decreases by one or more orders of magnitude. As fiber basis weight decreases, needling density may need to be increased.

The needling station 18 may be a "structuring loom" configured to subject the fiber layer 10 and carrier sheet 14 to a random velouring process. Thus, the needles penetrate a moving bed of bristles of the brush apron 22. The brush apron 22 may have a bristle density of about 2000 to 3000 bristles per square inch (310 to 465 bristles per square centimeter) (e.g., about 2570 bristles per square inch (400 per square centimeter)). The bristles are typically each about 0.018 inch (0.46 millimeter) in diameter and about 20 millimeters long, and are preferably straight. The bristles may be formed of 6/12 nylon or other suitable materials. Suitable brushes may be purchased from Stratosphere, Inc., a division of Howard Brush Co., and retrofitted onto DILO and other random velouring looms. Generally, the brush apron moves at the desired line speed.

As discussed below with respect to FIGS. 2A-2D and 3, the forked needles 34 to be used in the needling station 18 are typically selected based on the size of the larger, second fibers of the fiber layer 10, or vice versa, to ensure that the larger, second fibers 12b are too large to be captured by the needles 34, so that substantially only the smaller, first fibers 12a are typically needled through the carrier sheet 14 by the needles 34. More specifically, the width of a recess formed between tines of the forked needles 34 is typically less than about 110 percent (e.g., less than about 100 percent, less than about 90 percent, 50-110 percent, 50-100 percent, 50-90 percent) of the mean diameter of the second fibers 12b that are used or, in the case of second fibers 12b that do not have a circular cross-section, less than about 110 percent (e.g., less than about 100 percent, less than about 90 percent, 50-110 percent, 50-100 percent, 50-90 percent) of the diameter of the smallest imaginary circle capable of circumscribing one of those second fibers 12b.

Figure 2A:
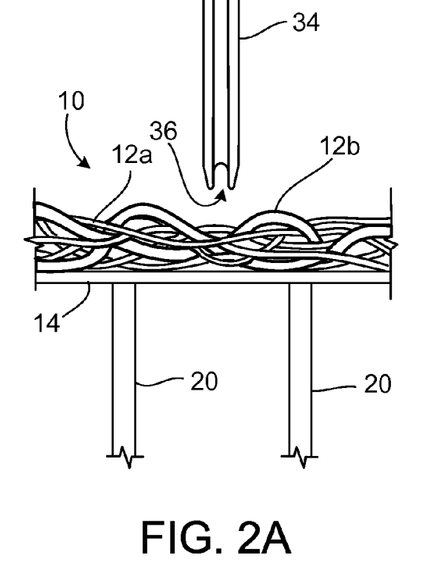
FIGS. 2A-2D are diagrammatic, cross-sectional side views of stages of a needling step of the process of FIG. 1.

FIGS. 2A through 2D sequentially illustrate the formation of a loop structure by needling. Referring to FIG. 2A, during the needling process, a forked needle 34 of the needling station 18 is moved downward toward the fiber mat 10 including both the smaller, first fibers 12a and the larger, second fibers 12b.

Figure 2B:
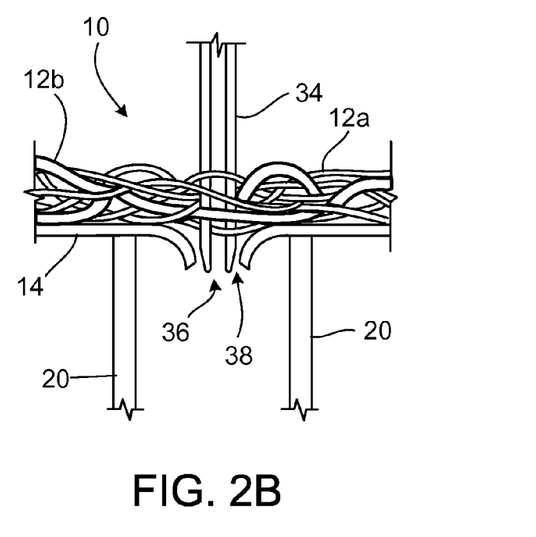

As the needle 34 pierces the carrier sheet 14, as shown in FIG. 2B, some of the smaller, first fibers 12a are captured in a recess 36 formed between two tines in the forked end of the needle 34 and the captured first fibers 12a are drawn with the needle 34 through a hole or opening 38 formed in the carrier sheet 14 to the other side (e.g., the front side) of the carrier sheet 14. However, due to the size of the larger second fibers 12b, the recess 36 of the forked needle 34 does not capture the larger fibers 12b. The carrier sheet 14 remains generally supported by bristles 20 of the brush apron 22 through this process, and the penetrating needle 34 enters a space between adjacent bristles 20.

Figure 2C:
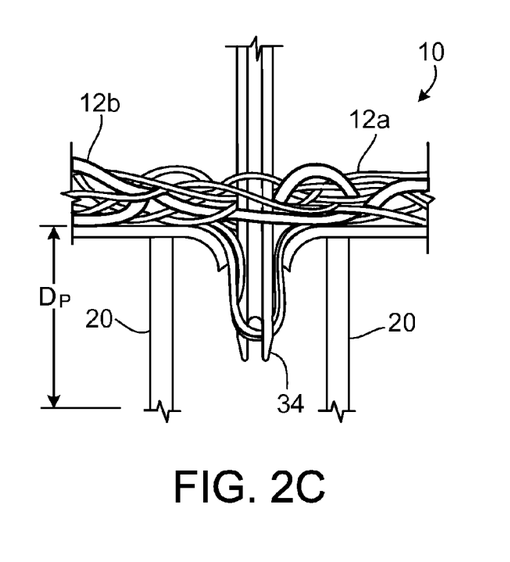

As the needle 34 continues to penetrate the carrier sheet 14 and fiber mat 10, as shown in FIG. 2C, tension is applied to the captured first fibers 12a, drawing the fiber mat 10 down against the carrier sheet 14. Typically, the needles 34 are operated in a manner to achieve a total penetration depth "$D_P$" of 3.0 to 12.0 millimeters (e.g., 4.0 to 6.0 millimeters), as measured from the entry surface of carrier sheet 14. As shown, the needles 34 used to push the first fibers 12a through the carrier sheet 14 each have a recess 36 that is sized and configured to allow multiple first fibers 12a to be captured and to prevent second fibers 12b to be typically captured by each needle when the needles 34 penetrate through the fiber mat 10 and the carrier sheet 14. Penetration depths in this range have been found to provide a well-formed loop structure without overly stretching fibers in the remaining fiber mat. Excessive penetration depth can draw loop-forming fibers from earlier-formed tufts, resulting in a less robust loop field.

Figure 2D:
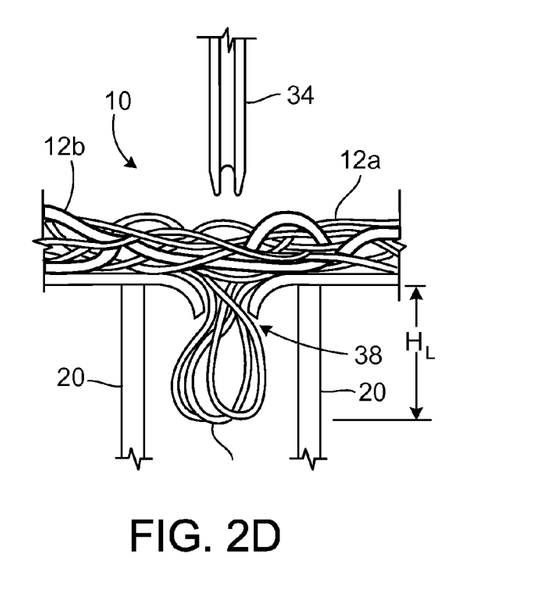

When the needle 34 is retracted from the carrier sheet 14 and fiber mat 10, as shown in FIG. 2D, the portions of the captured first fibers 12a carried to the opposite side of the carrier sheet 14 remain in the form of individual loops 40 that form a loop cluster trapped in the hole 38 formed in the carrier sheet 14. The loops typically have an overall height "$H_L$" of about 3.5 to 6.0 millimeters for engagement with commonly sized hook-like fastener elements.

Figure 3:
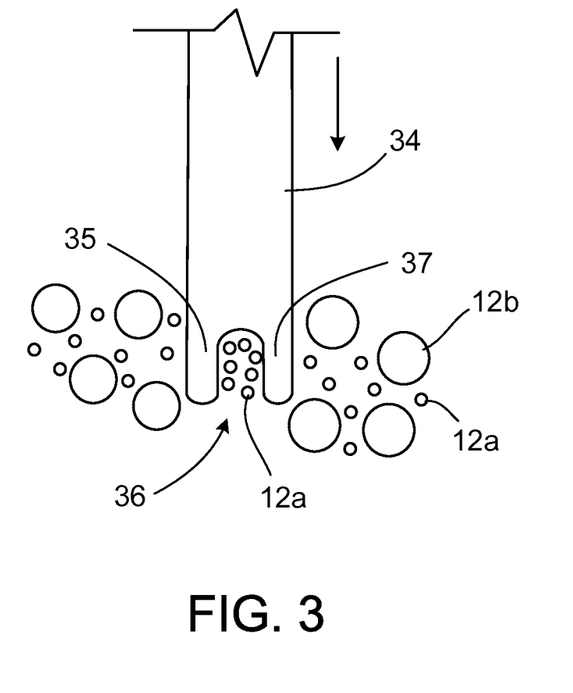
FIG. 3 is an enlarged view of a needle fork capturing fibers during the needling process illustrated in FIGS. 2A-2D.

FIG. 3 is an enlarged schematic illustration showing one of the needles 34 penetrating the fiber layer 10 in a manner so that only the smaller, first fibers 12a are captured in the recess 36 formed between tines 35 and 37 of the needle 34. Due to the size of the larger, second fibers 12b, the second fibers 12b that may be present near the needle 34 tend to be deflected away from the needle 34 since they are either too large to be captured or large enough that the likelihood of being captured is low. In order to capture substantially only the first fibers 12a during needling, the recess 36 is sized to have a width and a depth that are less than approximately 110 percent (e.g., less than about 100 percent, less than about 90 percent, 50-110 percent, 50-100 percent, 50-90 percent) of the average diameter of the second fibers 12b. For example, a 40 gauge forked needle having a 70 micron recess, as measured between the inner surfaces of the two tines, can be used to avoid capturing 30 dpf round fibers that have an average diameter of 65 microns. Although it is understood that such a sized second fiber 12b could fit into the recess under ideal alignment conditions, typically the lack of fiber alignment with the recess prevents the second fiber 12b from being captured in the recess 36 during needling. Due to the standard sizing of forked needles and fibers, other combinations of fibers and needles can be utilized.

By capturing only the smaller, first fibers 12a and preventing the larger, second fibers 12b from being captured when the forked needle fully penetrates the fiber mat 10 and the carrier sheet 14, a significant number (e.g., all or almost all) of the larger, second fibers 12b remain on the back side of the carrier sheet 14. Leaving the second fibers 12b, which are subsequently used for bonding during lamination, on the backside of the carrier sheet 14 allows for better, more even bonding and anchoring of the loops formed of the smaller, first fibers 12a that protrude from the front side of the carrier sheet 14. This technique also helps to ensure that the needled loops are adequately anchored while preventing excessive amounts of bonding material, such as bonding fibers, binding materials, etc., from being used which produces a more drapeable and less expensive product, as described below.

Referring again to FIG. 1, the needled web 88 leaves the needling station 18 and brush apron 22 in an unbonded state, and proceeds to a lamination station 92. Prior to reaching the lamination station 92, the needled web 88 passes over a gamma gage that provides a rough measure of the mass per unit area of the web. This measurement can be used as feedback to control the upstream carding and cross-lapping operations to provide more or fewer fibers based on the mass per unit area. Although the needled web 88 is in an unbonded state, it is stable enough to be accumulated in an accumulator 90 between the needling station 18 and the lamination station 92.

Figure 4:
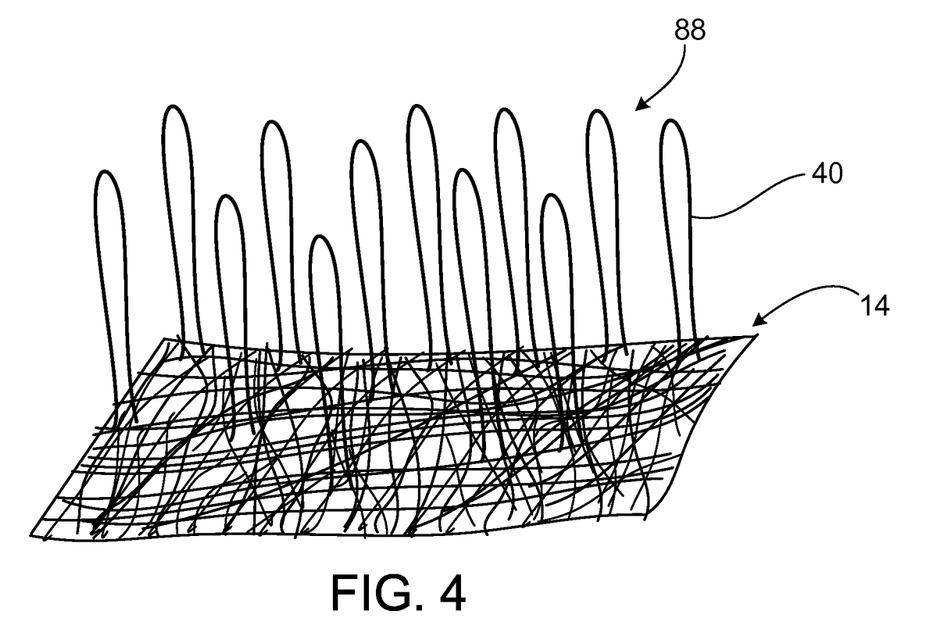
FIG. 4 is a schematic illustration of the front (loop) surface of a needled loop material, showing loop structures formed by needling first staple fibers from the back surface of the material during the process of FIG. 1.

FIG. 4 shows the needled web 88 that leaves the needling station 18. The needled web 88 has multiple loops 40 of first fibers 12a extending through the carrier sheet 14. As shown, the loops 40 are formed substantially only of the smaller, first fibers 12a due to the selective needling process that prevents the second fibers 12b from being needled through the carrier sheet 14. Typically, fewer than 20 (e.g., about 8 to about 12) of the second fibers are needled per square inch during needling, resulting in a needled web having no more than 10 percent of a total number of loops formed of second fibers (or a combination of first and second fibers) needled through the substrate. Testing has shown that when needling 3.3 dtex first fibers having a diameter of 17 microns and 30 dtex second fibers having a diameter of 65 microns, an average of 9.7 loops per square inch were formed of the second fibers.

The vertical stiffness of the loops can act to resist permanent crushing or flattening of the loop structures during subsequent processing steps when the loop material is laminated, or flattening of the loops when the finished product is later joined to a hook product and compressed for packaging. For example, the resiliency of the loops 40, especially at their juncture with the carrier sheet 14, enables loops 40 that have been "toppled" by heavy crush loads to right themselves when the load is removed.

Figure 5:
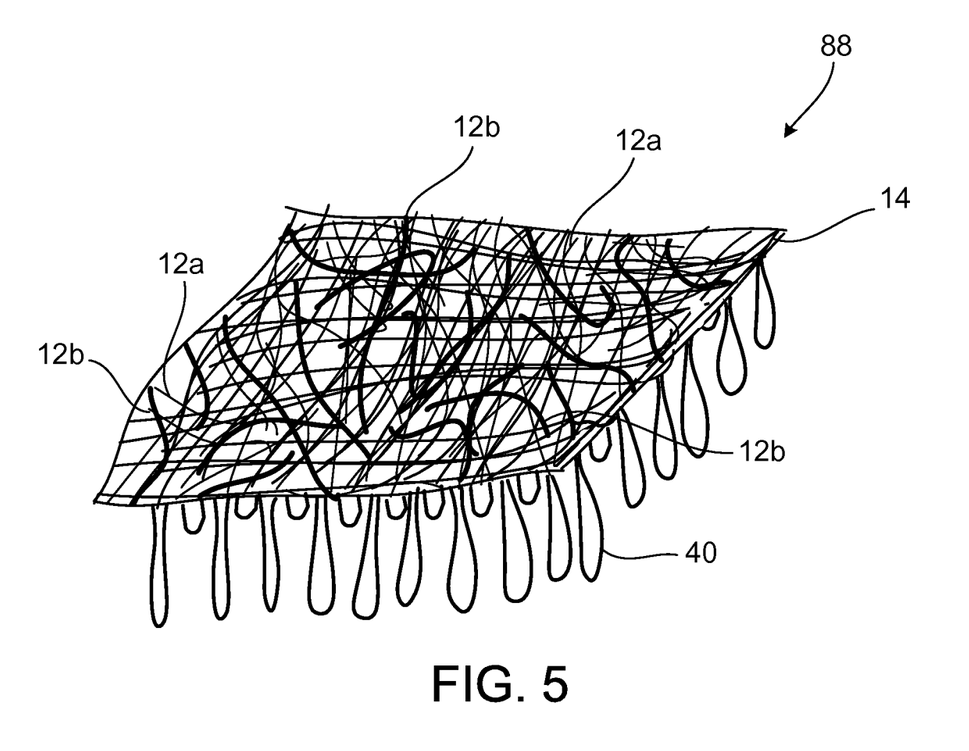
FIG. 5 is a schematic illustration of the back surface of the needled loop material formed during the process of FIG. 1, showing second fibers used for bonding remaining on the back surface.

As shown in FIG. 5, the back surface of the needled web 88 is relatively flat, void of extending loop structures, and includes substantially all of the second fibers 12b, which were not needled through the carrier sheet 14. Forming loop material in this manner reduces the amount of bonding fibers required and thus reduces the overall material required during lamination. Reducing the amount of material required and used for lamination advantageously reduces the overall cost of the loop product and can increase its drapeability.

Referring back to FIG. 1, after leaving the accumulator 90, the needled web 88 passes through a spreading roll that spreads and centers the needled web 88 prior to entering the lamination station 92. In the lamination station 92, the needled web 88 passes by one or more infrared heaters 94 that preheat the fibers 12a, 12b and/or the carrier sheet 14 from the side opposite the loops. The heater length and line speed are such that the needled web 88 spends about four seconds in front of the infrared heaters 94. Two scroll rolls 93 are positioned just prior to the infrared heaters 94. The scroll rolls 93 each have a herringbone helical pattern on their surfaces and rotate in a direction opposite to the direction of travel of the needled web 88, and are typically driven with a surface speed that is four to five times that of the surface speed of the needled web 88. The scroll rolls 93 put a small amount of drag on the material, and help to dewrinkle the needled web 88. Just downstream of the infrared heaters 94 is a web temperature sensor that provides feedback to the heater control to maintain a desired web exit temperature.

During lamination, the heated, needled web 88 is trained about a 20 inch (50 centimeter) diameter hot can 96 against which four idler rolls 98 of five inch (13 centimeter) solid diameter, and a driven, rubber roll 100 of 18 inch (46 centimeter) diameter, rotate under controlled pressure. Idler rolls 98 are optional and may be omitted if desired. Alternatively, light tension in the needled web 88 can supply a light and consistent pressure between the needled web 88 and the hot can 96 surface prior to the nip with rubber roll 100, to help to soften the bonding fiber surfaces prior to lamination pressure. The rubber roll 100 presses the needled web 88 against the surface of hot can 96 uniformly over a relatively long 'kiss' or contact area, bonding the fibers over substantially the entire back side of the web.

The rubber roll 100 is cooled, as discussed below, to prevent overheating and crushing or fusing of the loop fibers on the front surface of the needled web 88, thereby allowing the loop fibers to remain exposed and standing upright to maintain the hook-engageability of the loops. The bonding pressure between the rubber roll 100 and the hot can 96 is typically quite low. The bonding pressure can, for example, be in the range of about 1-50 pounds per square inch (psi) (70-3500 gsm) or less (e.g., about 15 to 40 psi (1050 to 2800 gsm), about 25 psi (1750 gsm)). In order to bond the fibers 12b and carrier sheet 14, the surface of the hot can 96 is typically maintained at a temperature of about 306 degrees Fahrenheit (150 degrees Celsius). The needled web 88 is trained about an angle of around 300 degrees around the hot can 96, resulting in a dwell time against the hot can of about four seconds to avoid overly melting the needled web. The hot can 96 can have a compliant outer surface, or be in the form of a belt.

Figure 6:
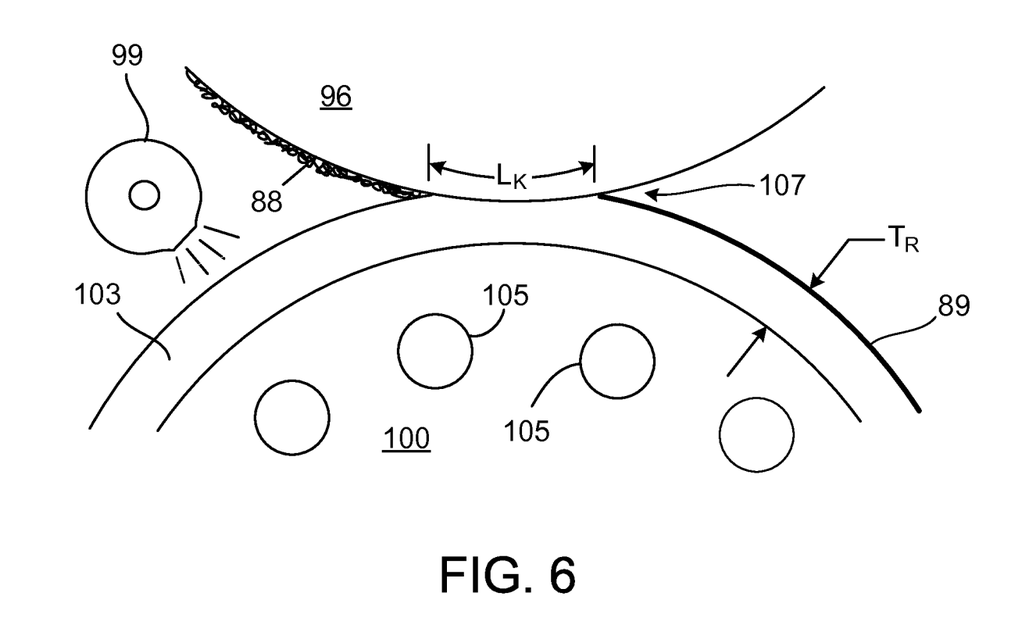
FIG. 6 is an enlarged diagrammatic view of a lamination nip through which the loop material passes during the process of FIG. 1.

FIG. 6 is an enlarged view of the nip 107 between hot can 96 and the rubber roll 100. As discussed above, due to the compliant nature of the rubber roll 100, uniform pressure and heat are applied to the entire back surface of the needled web 88, over a relatively large contact area. The hot can 96 contacts the fibers on the back side of the needled web 88 to fuse the fibers to each other and/or to fibers of the non-woven carrier sheet 14, forming a network of fused fibers extending over the entire back surface of the carrier sheet 14. The surface of the hot can 96, as noted above, is typically maintained at a temperature of about 306 degrees F. (150 degrees C.). The rubber roll 100 includes a rubber surface layer 103 that is positioned about and supported by a cooled steel core. The rubber surface layer 103 has a radial thickness $T_R$ of about 22 millimeters, and has a surface hardness of about 65 Shore A. Nip pressure is typically maintained between the rolls such that the nip kiss length $L_k$ about the circumference of hot can 96 is about 25 millimeters, with a nip dwell time of about 75 milliseconds. Leaving the nip, a laminated web 89 travels on the surface of the cooled roll 100. To cool the cooled rolled 100, liquid coolant is circulated through cooling channels 105 in the steel core to maintain a core temperature of about 55 degrees F. (12.7 degrees C.) while an air plenum 99 discharges multiple jets of air against the rubber roll surface to maintain a rubber surface temperature of about 140 degrees F. (60 degrees C.) entering nip 107.

Figure 7:
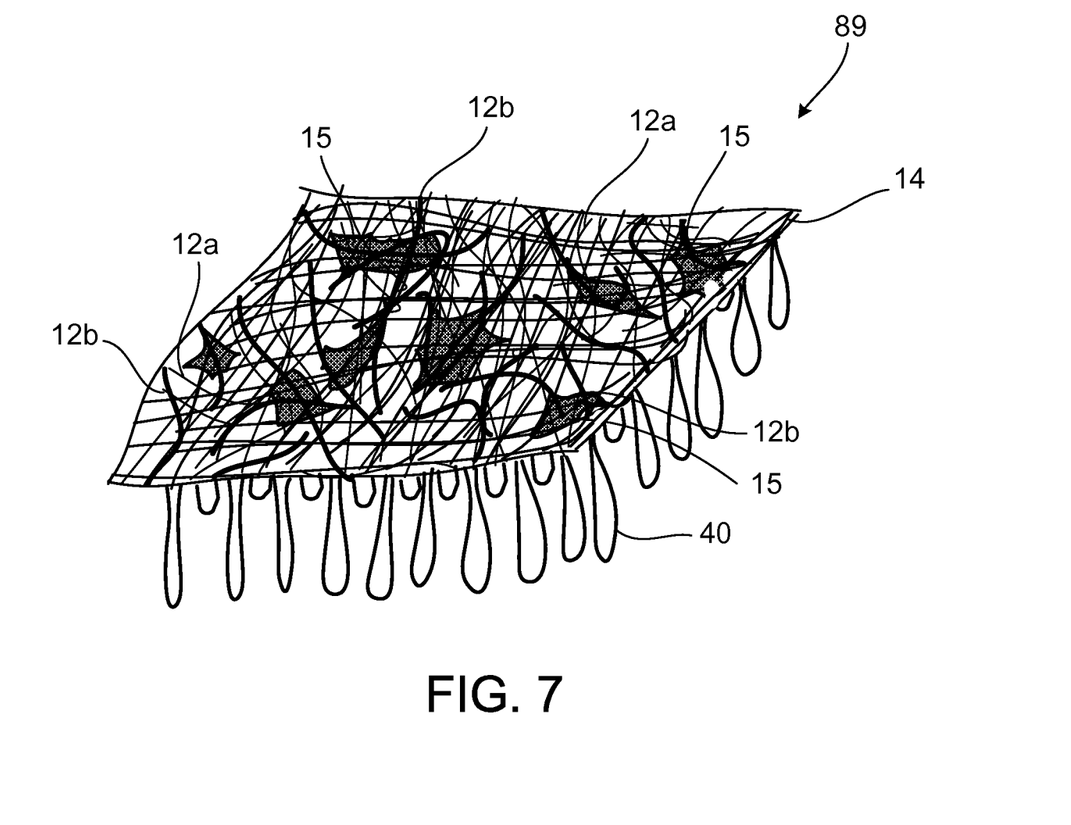
FIG. 7 is a schematic illustration of the back surface of a laminated needled loop material formed during the process of FIG. 1, showing a network of bonding sites.

The back surface of the loop material leaving the nip (i.e., the laminated web 89) is fused and relatively flat. During lamination, the individual first fibers tend to maintain their longitudinal molecular orientation through bonding sites 15 that are formed by the melted second fibers 12b. As shown in FIG. 7, a formed network of bonding sites 15 is relatively random and sufficiently dense to effectively anchor the first fiber portions extending through the non-woven carrier sheet to the front side to form engageable loop formations. However, the network of bonding sites 15 is typically not so dense that the laminated web 89 becomes air-impermeable, or overly stiff or heavy. Due to the distribution of bonding sites 15, the resulting loop fastener product will typically have a soft hand and working flexibility for use in applications where textile properties are desired. In other applications it may be acceptable or desirable to fuse the fibers to form a solid mass on the back side of the laminated web 89. The fused network of bonding sites 15 creates a very strong, dimensionally stable laminated web 89 of fused fibers across the non-working side of the laminated web 89 that is still sufficiently flexible for many uses and allows the loops to move during use without undue rigidity. In either case, fewer bonding fibers are required, thereby reducing the cost and, in many cases, increasing the drapeability of the resulting loop product.

Referring back to FIG. 1, from the lamination station 92, the laminated web 89 moves through another accumulator 90 and on to an embossing station 104 where, between two counter-rotating embossing rolls, a desired pattern of locally raised regions is embossed into the laminated web 89 to form an embossed web 91. In some cases, the laminated web 89 may move directly from the lamination station 92 to the embossing station 104, without accumulation, so as to take advantage of any latent temperature increase caused by the laminating process. As shown in FIG. 1, the laminated web 89 is passed through a nip between a driven embossing roll 54 and a backup roll 56. The embossing roll 54 has a pattern of raised areas that permanently crush the loops against the carrier sheet, and may even melt a portion of the fibers in those areas. Embossing may be employed simply to enhance the texture or aesthetic appeal of the final product. Generally, the laminated web 89 has sufficient strength and structural integrity so that embossing is not needed to (and typically does not) enhance the physical properties of a resulting embossed web (e.g., the loop fastener product 31).

In some cases, the backup roll 56 has a pattern of raised areas that mesh with dimples in the embossing roll 54, such that embossing results in a pattern of raised hills or convex regions on the front side, with corresponding concave regions on the non-working side of the laminated web 89, such that the embossed web 91 has a greater effective thickness than the pre-embossed laminated web 89.

Figure 8:
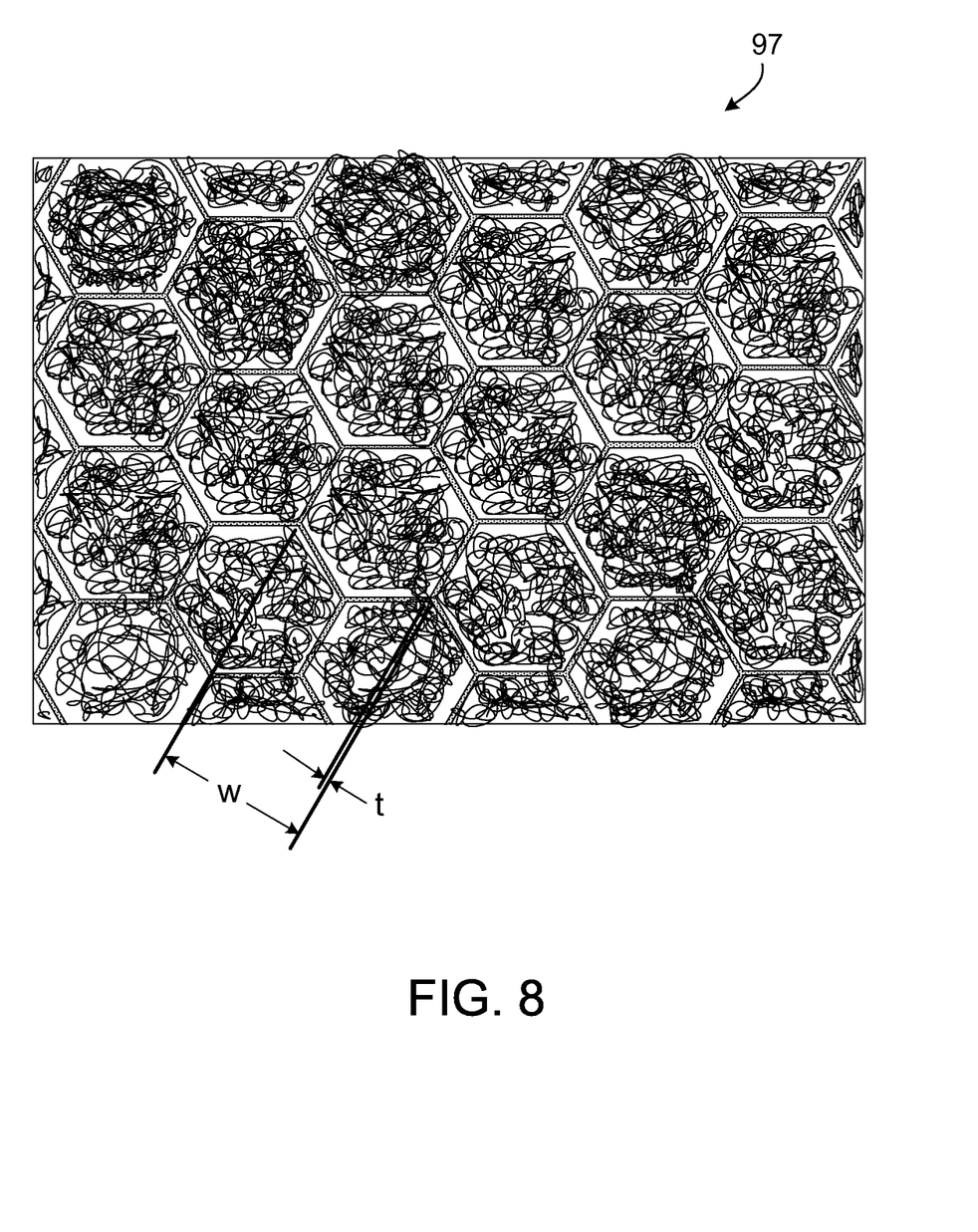
FIG. 8 is a plan view of a front surface of a loop material having an embossed pattern on its front surface imparted by an embossing station during the process of FIG. 1.

As shown in FIG. 8, by way of an example, each cell of the embossing pattern in the embossed web 91 is a closed hexagon and contains multiple discrete loops. The width 'W' between opposite sides of the open area of the cell is about 6.5 millimeters, while the thickness T of the wall of the cell is about 0.8 millimeter. Various other embossing patterns can be created, for example, a grid of intersecting lines forming squares or diamonds, or a pattern that crushes the loops other than in discrete regions of a desired shape, such as round pads of loops. The embossing pattern may also crush the loops to form a desired image, or text, on the loop material.

Referring back to FIG. 1, from the embossing station 104, the loop fastener product 31 moves through a final accumulator 90 and past a metal detector 106 that checks for any broken needles or other metal debris that could become lodged in the fastener product during manufacturing. After passing by the metal detector 106, the loop fastener product 31 is slit to desired final widths and spooled for storage or shipment. During slitting, edges may be trimmed and removed, as can any undesired carrier sheet overlap region necessitated by using multiple parallel strips of carrier sheet.

While certain embodiments have been described, other embodiments are possible.

While certain processes discussed above have been described as using first fibers that are 3 denier per filament (dpf) non-bonding polyester fibers having a mean diameter of approximately 17 microns and second fibers that are 27 dpf bonding polypropylene fibers having a mean diameter of approximately 65 microns along with 40 gauge forked needles having a recess that is 70 microns wide to avoid capturing the second fibers, other combinations of fiber sizes and materials, and needles are possible. In some embodiments, 6.6 dpf first fibers and 27 dpf second fibers are used.

In some embodiments, the smaller first fibers have a diameter of 15-35 microns so that they can be captured by the forked needle during needling. In certain embodiments, the larger second fibers have a diameter of 60-350 microns so that they are not captured by the forked needle during needling.

The fibers can be made of various materials including polyolefins, polyesters, polyamides, and acrylics or mixtures, alloys, copolymers and/or co-extrusions of polyolefins, polyesters, polyamides, and acrylics. Although many types of fiber materials can be used, the fiber materials are chosen so that the melting temperature of the first fibers is higher than the melting temperature of the second fibers so that the second fibers can melt during lamination while the first fibers typically do not.

Although the needling station has been described as including 40 gauge forked needles having a recess width of 70 microns, other needles having a larger recess can be used. For example, in some embodiments, 42, 40, 38, 36, 30, 25, 20, 19, or 17 gauge forked needles having recess widths of 50-500 microns are used to capture the first fibers and not capture the second fibers. As discussed above, the needle to be used will typically depend on the size of the fibers to be needled. In many cases, the needles will be sized to ensure that the second fibers are typically not captured in the recess of each needle.

Although the needling station has been described as including only one type of needle, combinations of different types of needles can be used. In some embodiments, the needling station includes needles are sized to prevent needling the larger, second fibers through the carrier sheet and some other needles that are sized to enable needling the second, larger fibers.

Although the first and second fibers have been described as being provided in fiber blend having a 4:1 mass ratio of first fibers to second fibers, other blends of fibers are possible. For example, in some embodiments, the blend of first and second fibers are provided in mass ratios of 3:1 to 1:1, first fibers to second fibers. Although the systems above have been described as including one needling station, the systems can alternatively include additional needle stations. For example, in some embodiments, the system includes two or more (e.g., 2, 3, 4, 5, 6, 7, or more) needling stations having needle looms that are used to needle fibers through the carrier sheet. In some embodiments, each needling station includes more than one (e.g., 2, 4, or more) needle boards. Systems including multiple needling stations and/or multiple needle boards per needling station allow for needles of different sizes (e.g., different heights, different gauges, etc.) to be used during the needling process to provide different types of loops or loop clusters in the resulting loop material.

Although the needling station has been described as including a bed of bristles extending from a driven support belt of brush apron that moves with the carrier sheet, other types of supports can be used. In some embodiments, the carrier sheet can be supported by a screen or stitching plate that defines holes aligned with the needles.

While many of the embodiments discussed above describe capturing none of the larger, second fibers in each needle, in certain implementations, the needles capture some of the second fibers in the needle recess. Even in the event that some of the second fibers are needled through the substrate, selecting the forked needles based on the size of the second fibers or vice versa reduces the number of second fibers that are needled through the substrate and thus increases the amount of second fibers exposed on the back side of the substrate for bonding.

Although the lamination station has been described as including hot roller nips, other types of laminators can be used. In some embodiments, for example, a flatbed fabric laminator is used to apply a controlled lamination pressure for a considerable dwell time. Such flatbed laminators are available from Glenro Inc. in Paterson, N.J.

Although the lamination station has been described as including a hot can 96 with a surface that is typically maintained at a temperature of about 306 degrees F. (150 degrees C.), other lamination temperatures are possible. The laminating station operating temperature generally exceeds the melting temperature of the selected second fiber material, but is typically less than the melting temperature of the first fibers to ensure that the first fibers are properly anchored but not melted on the front side of the carrier sheet.

In certain embodiments, the finished loop product is passed through a cooler after lamination.

Although the process above has been described as including accumulators between various stations, in some cases, web material can move directly between stations without accumulation. In some embodiments, no accumulators are included between any of the various stations.

Although the first and second fibers have been described as being cylindrical or having a round cross-sectional profile, other fiber shapes can be used. In some embodiments, the fibers have a cross-sectional profile including polygon-shaped profiles (e.g., triangles, rectangles, pentagons, hexagons), polygons having curved sides-shaped profiles (e.g., Reuleaux polygons), or polylobal-shaped profiles. When such non-cylindrical fibers are used, instead of being sized to match the diameter of the second fibers, the recess of the forked needle is sized to match the diameter of a smallest imaginary circle that could circumscribe the cross-sectional profile of the second fibers.

Figure 9:
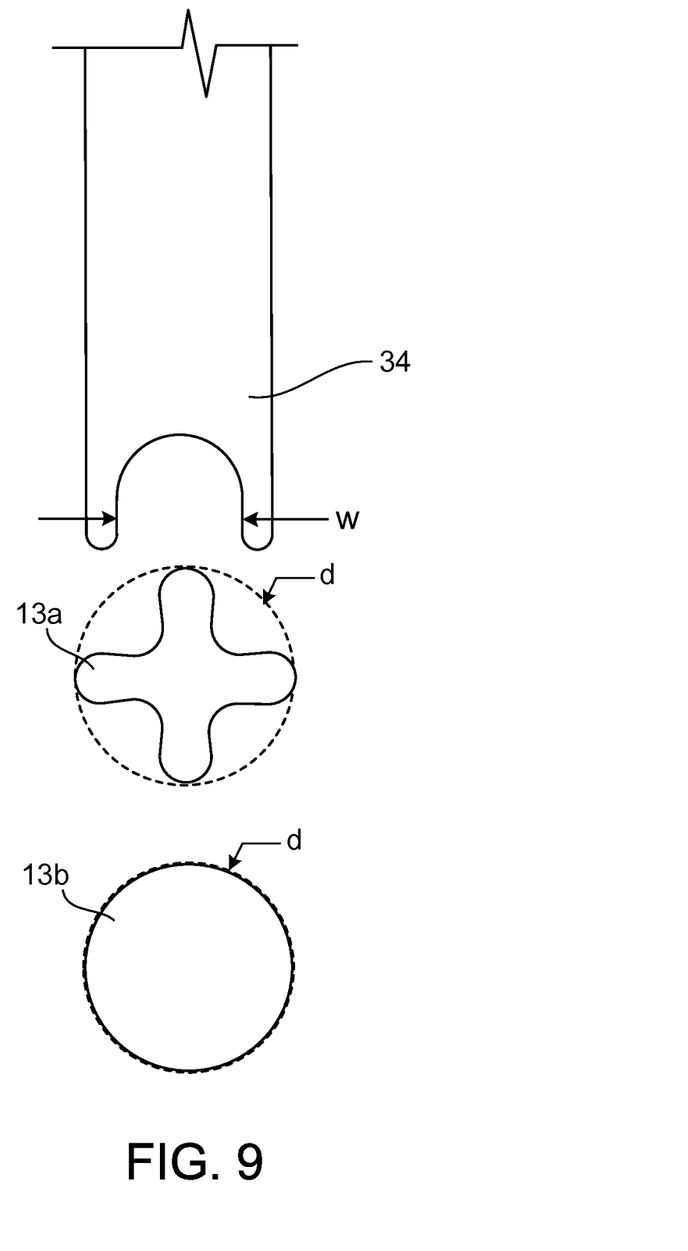
FIG. 9 is a diagrammatic cross-sectional view of different shaped bonding fibers that can be used to form the loop material resulting from the process of FIG. 1.

FIG. 9 shows an example of a smallest imaginary circle (shown in dashed lines) having a diameter d that circumscribes the cross-sectional profile of a non-cylindrical fiber (e.g., a quadrilobe fiber shaped fiber) 13a and a cylindrical fiber 13b to avoid being captured by a forked needle 34 having a recess width w. As shown, when cylindrical fibers 13b are used, the diameter d of the smallest imaginary circle that circumscribes the cross-sectional profile of the cylindrical fiber 13b is equal to the diameter of the cylindrical fibers 13b. As discussed above, a width w of the recess of the forked needle 34 can be selected based on the diameter d of the fiber or fibers to be used. The diameter d can, for example, be at least about 90 percent (e.g., at least about 100 percent, about 90-150 percent, about 100-150 percent) of the width w to ensure that the second fibers 12b are not needled through the substrate.

Although the carrier sheet has been described as being a spunbond web made from a polymer, other materials may alternatively or additionally be used. For example, in some embodiments, the carrier sheet is formed of a thin film, paper, a textile such as scrim, a lightweight cotton sheet, or another non-woven, woven, or knit material.

In some embodiments, the carrier sheet is point bonded. The spunbond web may include a non-random pattern of fused areas, each fused area being surrounded by unfused areas. The fused areas may have any desired shape, e.g., diamonds or ovals, and are generally quite small, for example on the order of several millimeters.

In some embodiments, a pre-printed carrier sheet may be employed to provide graphic images visible from the front side of the finished product. This can be advantageous, for example, for loop fastener materials to be used on children's products, such as disposable diapers. In such cases, child-friendly graphic images can be provided on the hook-engageable material that is permanently bonded across the front of the diaper chassis to form an engagement zone for the diaper tabs. The image can be pre-printed on either surface of the carrier sheet, but is generally printed on the front side. An added film may alternatively be pre-printed to add graphics, particularly if acceptable graphic clarity cannot be obtained on a lightweight carrier sheet such as a spunbond web.

Although the processes above have been described as including embossing the loop fastener material to provide a textured pattern on the fastener material, in some embodiments, the resulting loop fastener material is not embossed.

Although the processes above have been described as including slitting the material into smaller rolls, in some embodiments, the fastener material is undivided and remains as large rolls. Undivided, larger rolls can be used for applications requiring a fastener material having a large surface area (e.g., for fastening home siding or roofing material). In some cases, large rolls can be up to 2-3 meters wide.

While the second staple fibers have been described as being melted to themselves, to the first fibers and to the carrier sheet during lamination, in some embodiments, a binder can be used to anchor the fibers. The binder may be applied in liquid or powder form, and may even be pre-coated on the fiber side of the carrier web before the fibers are applied. Alternatively or additionally, if desired, a backing sheet can be introduced between the hot can and the needled web, such that the backing sheet is laminated over the back surface of the needled web while the fibers are bonded under pressure in the nip.

Polymer backing layers or binders may be selected from among suitable polyethylenes, polyesters, EVA, polypropylenes, and their co-polymers.

In some cases, advance per stroke of the needles may be limited due to a number of constraints, including needle deflection and potential needle breakage. Thus, it may be difficult to accommodate increases in line speed and obtain an economical throughput by adjusting the advance per stroke. As a result, the holes pierced by the needles may become elongated, due to the travel of the carrier sheet while the needle is interacting with the carrier sheet (the "dwell time"). This elongation is generally undesirable, as it reduces the amount of support provided to the base of each of the loop structures by the surrounding substrate, and may adversely affect resistance to loop pull-out. Moreover, this elongation will tend to reduce the mechanical integrity of the carrier sheet due to excessive drafting (i.e., stretching of the carrier sheet in the machine direction and corresponding shrinkage in the cross-machine direction).

Figure 10:
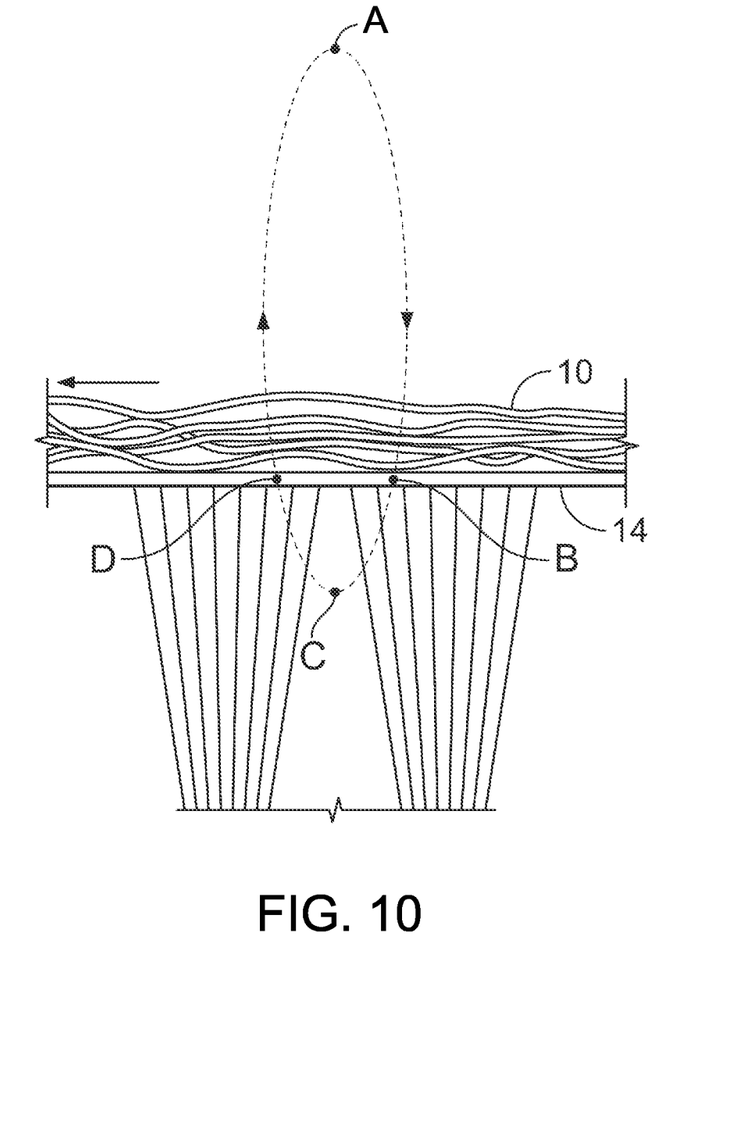
FIG. 10 is a diagrammatic side view of an elliptical needling process that can be used to needle fibers through a substrate during a process of forming hook-engageable loop fastener material.

Elongation of the holes may be reduced or eliminated by moving the needles in a generally elliptical path (e.g., when viewed from the side). This elliptical path is shown schematically in FIG. 10. As shown in FIG. 10, each needle begins at a top "dead center" position A, travels downward to pierce the carrier sheet (position B) and, while it remains in the carrier sheet (from position B through bottom "dead center" position C to position D), moves forward in the machine direction. When the needle has traveled upward sufficiently for its tip to have exited the pierced opening (position D), it continues to travel upward, free of the carrier sheet, while also returning horizontally (opposite to the machine direction) to its normal, rest position (position A), completing the elliptical path. This elliptical path of the needles is accomplished by moving the entire needle board simultaneously in both the horizontal and vertical directions. Needling in this manner is referred to herein as "elliptical needling." Needling looms that perform this function are available from DILO System Group, Eberbach, Germany, under the tradename "HYPERPUNCH Systems."

During elliptical needling, the horizontal travel of the needle board is generally a function of needle penetration depth, vertical stroke length, carrier sheet thickness, and advance per stroke, and is typically roughly equivalent to the distance that the carrier sheet advances during the dwell time. Generally, at a given value of needle penetration and carrier sheet thickness, horizontal stroke increases with increasing advance per stroke. At a fixed advance per stroke, the horizontal stroke generally increases as depth of penetration and web thickness increases.

While the process above has been described as including a first carding station, a cross-lapper, and a second carding station, other fiber preparation components and/or methods can be used. In some embodiments, instead of a first carding station and a cross lapper, a fiber bale opening machine and a fiber blending machine are used to prepare fibers and provide them to a single carding station.

While embodiments discussed above describe the formation of relatively short loop-engageable fastener elements, it should be understood that fastener elements of any of various sizes can be formed using the processes described herein.

In some embodiments, the materials of the loop fastener product are selected for other desired properties. In some cases, the loop fibers, carrier web, and backing are all formed of polypropylene, making the finished loop fastener product readily recyclable. In another example, the loop fibers, carrier web and backing are all of a biodegradable material, such that the finished loop product is more environmentally friendly. High tenacity fibers of biodegradable polylactic acid are available, for example, from Cargill Dow LLC under the trade name NATUREWORKS.

Other embodiments are within the scope of the following claims.

What is claimed is:

1. A method of making a sheet-form loop product, the method comprising
   placing a layer of staple fibers on a first side of a substrate, the layer of staple fibers comprising first staple fibers and second staple fibers that are intermingled with one another, wherein a diameter of the smallest circle capable of circumscribing one of the second staple fibers is greater than a diameter of the smallest circle capable of circumscribing one of the first staple fibers;
   needling substantially only the first fibers of the layer through the substrate by penetrating the substrate with needles that drag portions of the first fibers through the substrate during needling, leaving exposed loops of the first fibers extending from a second side of the substrate; and
   anchoring the loops of the first fibers by fusing the second fibers to each other on the first side of the substrate.

2. The method of claim 1, wherein the needles are forked needles having a recess width configured to inhibit the second fibers from being needled through the substrate.

3. The method of claim 2, wherein the recess width is less than 110 percent of the diameter of the smallest circle capable of circumscribing one of the second staple fibers.

4. The method of claim 2, wherein the diameter of the smallest circle capable of circumscribing one of the second staple fibers is at least about 90 percent of the recess width of the needles.

5. The method of claim 1, wherein the diameter of the smallest circle capable of circumscribing one of the first staple fibers is about 15-35 microns.

6. The method of claim 1, wherein the diameter of the smallest circle capable of circumscribing one of the second staple fibers is about 50-75 microns.

7. The method of claim 1, wherein the needles are 38-42 gauge forked needles.

8. The method of claim 1, wherein the layer of staple fibers comprises no more than 50 percent of second fibers.

9. The method of claim 1, wherein no more than 20 second fibers per square inch are needled through the substrate.

10. The method of claim 1, wherein a total number of loops formed on the second side of the substrate comprises no more than 10 percent loops formed of second fibers.

11. The method of claim 1, further comprising selecting needles based on the first and second staple fibers of the layer of staple fibers to be placed on the substrate.

12. The method of claim 1, wherein the melting temperature of the first fibers is higher than the melting temperature of the second fibers.

13. The method of claim 1, wherein anchoring the loops comprises melting the second fibers.

14. The method of claim 1, wherein anchoring the loops comprises bonding the second fibers to portions of the first fibers and to the substrate.

15. The method of claim 1, wherein the first fibers and second fibers are not fixed to the substrate or each other until needled.

16. The method of claim 1, wherein needling substantially only the first fibers through the substrate and anchoring fibers forming the loops forms loops sized and constructed to be releasably engageable by a field of hooks for hook-and-loop fastening.

17. The method of claim 1, wherein the substrate comprises a nonwoven web.

* * * * *